(12) United States Patent
Pruitt et al.

(10) Patent No.: US 9,348,061 B2
(45) Date of Patent: *May 24, 2016

(54) CONTACT LENS PRODUCTS

(71) Applicant: Novartis AG, Basel (CH)

(72) Inventors: John Dallas Pruitt, Suwanee, GA (US); Lynn Cook Winterton, Keller, TX (US)

(73) Assignee: Novartis AG, Basel (CH)

( * ) Notice: Subject to any disclaimer, the term of this patent is extended or adjusted under 35 U.S.C. 154(b) by 146 days.

This patent is subject to a terminal disclaimer.

(21) Appl. No.: 14/102,723

(22) Filed: Dec. 11, 2013

(65) Prior Publication Data

US 2014/0096484 A1  Apr. 10, 2014

Related U.S. Application Data

(62) Division of application No. 12/229,769, filed on Aug. 27, 2008, now Pat. No. 8,647,658.

(60) Provisional application No. 60/969,339, filed on Aug. 31, 2007.

(51) Int. Cl.
*A61L 12/04* (2006.01)
*G02B 1/04* (2006.01)
*B29D 11/00* (2006.01)
*A61K 9/00* (2006.01)

(52) U.S. Cl.
CPC ............. *G02B 1/043* (2013.01); *A61L 12/04* (2013.01); *B29D 11/00067* (2013.01); *A61K 9/0048* (2013.01)

(58) Field of Classification Search
CPC ........ G02B 1/043; A61L 27/18; A61L 12/14; A61L 27/34; A61L 12/08; A61L 27/26; A61L 12/141; A61L 31/10; A61L 12/142; A61L 29/085; A61L 12/143; A61L 12/00; A61L 27/52; A61L 12/147; A61L 27/54
See application file for complete search history.

(56) References Cited

U.S. PATENT DOCUMENTS

| | | | |
|---|---|---|---|
| 3,549,747 A | 12/1970 | Krezanoski et al. | 424/78 |
| 3,639,576 A | 2/1972 | Kaspar et al. | 424/78 |
| 3,882,036 A | 5/1975 | Krezanoski et al. | 252/106 |
| 4,013,576 A | 3/1977 | Loshaek | 134/42 |
| 4,287,175 A | 9/1981 | Katz | 424/78 |
| 4,323,467 A | 4/1982 | Fu | 252/106 |
| 4,440,662 A | 4/1984 | Tsuzuki et al. | 252/106 |
| 4,500,441 A | 2/1985 | Tanaka et al. | 252/89.1 |
| 4,529,535 A | 7/1985 | Sherman | 252/106 |
| 4,551,461 A | 11/1985 | Sherman | 514/275 |
| 4,560,491 A | 12/1985 | Sherman | 252/106 |
| 4,626,292 A | 12/1986 | Sherman | 134/26 |
| 4,746,514 A | 5/1988 | Warne | 424/445 |
| 4,783,488 A | 11/1988 | Ogunbiyi et al. | 514/635 |
| 4,786,436 A | 11/1988 | Ogunbiyi et al. | 252/352 |
| 4,808,239 A | 2/1989 | Schafer et al. | 134/42 |
| 5,036,971 A | 8/1991 | Seden et al. | 206/5.1 |
| 5,141,665 A | 8/1992 | Sherman | 252/106 |
| 5,157,093 A | 10/1992 | Harisiades et al. | 527/301 |
| 5,198,477 A | 3/1993 | vonderHaegen et al. | 523/106 |
| 5,260,001 A | 11/1993 | Nandu et al. | 264/2.1 |
| 5,310,429 A | 5/1994 | Chou et al. | 134/6 |
| 5,322,667 A | 6/1994 | Sherman | 422/28 |
| 5,364,601 A | 11/1994 | Salpekar | 422/28 |
| 5,382,599 A | 1/1995 | Rupp et al. | 514/547 |
| 5,405,878 A | 4/1995 | Ellis et al. | 422/28 |
| 5,500,144 A | 3/1996 | Potini et al. | 253/174.15 |
| 5,604,189 A | 2/1997 | Zhang et al. | 510/112 |
| 5,605,661 A * | 2/1997 | Asgharian et al. | 422/28 |
| 5,711,823 A | 1/1998 | Ellis et al. | 134/42 |
| 5,712,356 A | 1/1998 | Bothe et al. | 526/264 |
| 5,726,733 A | 3/1998 | Lai et al. | 351/160 |
| 5,731,087 A | 3/1998 | Fan et al. | 428/412 |
| 5,773,396 A | 6/1998 | Zhang et al. | 510/115 |
| 5,800,412 A | 9/1998 | Zhang et al. | 604/280 |
| 5,800,807 A | 9/1998 | Hu et al. | 424/78 |
| 5,807,636 A | 9/1998 | Sheu et al. | 428/403 |
| 5,837,377 A | 11/1998 | Sheu et al. | 428/412 |
| 5,872,086 A | 2/1999 | Ellis et al. | 510/112 |
| 5,882,687 A | 3/1999 | Park et al. | 424/682 |
| 5,942,558 A | 8/1999 | Korb | 523/106 |
| 5,985,629 A | 11/1999 | Aaslyng et al. | 435/174 |

(Continued)

FOREIGN PATENT DOCUMENTS

EP   0 315 836   10/1988
EP   1 187 873 B1   9/2004

(Continued)

OTHER PUBLICATIONS

English Translation of Office Action dated Apr. 2, 2013 in Japanese pending application 2010-522942.
English Translation of Office Action dated Jan. 24, 2013 in Chinese pending application 200880104708.4.
English Translation of Chinese Office Action dated Feb. 29, 2012; Chinese Patent Application No. 200880104708.4.

(Continued)

*Primary Examiner* — Audrea Buckley
(74) *Attorney, Agent, or Firm* — Jian Zhou

(57) ABSTRACT

The present invention relates to improved contact lens products which not only have initial insertion comfort but also are comfortable to wear for more than about 6 hours. The invention is achieved by packaging and storing a hydrogel lens with two or more leachable polymeric lubricants incorporated therein in a relatively viscous packaging solution including a relatively low molecular weight polyethylene glycol (PEG) and a viscosity-enhancing hydrophilic polymer. The present invention also provides methods for making contact lens products of the invention.

20 Claims, No Drawings

(56) References Cited

U.S. PATENT DOCUMENTS

| | | | |
|---|---|---|---|
| 5,998,498 A | 12/1999 | Vanderlaan et al. | 523/107 |
| 6,037,328 A | 3/2000 | Hu et al. | 514/23 |
| 6,121,327 A * | 9/2000 | Tsuzuki et al. | 514/642 |
| 6,136,850 A | 10/2000 | Park et al. | 514/458 |
| 6,193,369 B1 | 2/2001 | Valint, Jr. et al. | 351/160 |
| 6,207,628 B1 | 3/2001 | Soyer et al. | 510/112 |
| 6,258,591 B1 | 7/2001 | Yoneda et al. | 435/264 |
| 6,274,133 B1 | 8/2001 | Hu et al. | 424/78.04 |
| 6,338,847 B1 | 1/2002 | Thomas | 424/94.2 |
| 6,348,507 B1 | 2/2002 | Heiler et al. | 514/769 |
| 6,367,929 B1 * | 4/2002 | Maiden et al. | 351/159.33 |
| 6,428,839 B1 | 8/2002 | Kunzler et al. | 427/2.1 |
| 6,440,366 B1 | 8/2002 | Salpekar et al. | 422/40 |
| 6,482,799 B1 | 11/2002 | Tuse et al. | 514/14 |
| 6,511,949 B1 * | 1/2003 | Nitta et al. | 510/112 |
| 6,528,048 B1 | 3/2003 | Koike et al. | 424/78.17 |
| 6,531,432 B2 | 3/2003 | Molock et al. | 510/112 |
| 6,617,291 B1 | 9/2003 | Smith | 510/112 |
| 6,634,748 B1 | 10/2003 | Vanderlaan | 351/177 |
| 6,686,330 B2 | 2/2004 | Jordan et al. | 510/475 |
| 6,699,435 B2 | 3/2004 | Salpekar et al. | 422/40 |
| 6,702,983 B2 | 3/2004 | Hu et al. | 422/1 |
| 6,805,836 B2 | 10/2004 | Salamone et al. | 422/1 |
| 6,815,074 B2 | 11/2004 | Aguado et al. | 428/447 |
| 6,822,016 B2 | 11/2004 | McCabe et al. | 523/107 |
| 6,867,172 B2 | 3/2005 | Alvarez et al. | 510/112 |
| 6,926,965 B2 | 8/2005 | Qiu et al. | 428/411.1 |
| 7,037,469 B2 | 5/2006 | Hu et al. | 422/28 |
| 7,247,270 B2 | 7/2007 | Hu et al. | 422/28 |
| 2002/0018732 A1 | 2/2002 | Hung et al. | 422/28 |
| 2002/0071789 A1 | 6/2002 | Molock et al. | 422/112 |
| 2002/0115578 A1 | 8/2002 | Groemminger | 510/112 |
| 2002/0182315 A1 | 12/2002 | Heiler et al. | 427/162 |
| 2003/0052424 A1 | 3/2003 | Turner et al. | 264/1.32 |
| 2003/0095230 A1 | 5/2003 | Neely et al. | 351/159 |
| 2003/0096717 A1 | 5/2003 | Xia et al. | 510/112 |
| 2003/0125498 A1 | 7/2003 | McCabe et al. | 528/25 |
| 2003/0129083 A1 | 7/2003 | Graham et al. | 422/42 |
| 2003/0130144 A1 | 7/2003 | Alvarez et al. | 510/112 |
| 2003/0162862 A1 | 8/2003 | McCabe et al. | 523/106 |
| 2004/0014829 A1 | 1/2004 | Neff | |
| 2004/0028645 A1 | 2/2004 | Chowhan | 424/78.27 |
| 2004/0116564 A1 | 6/2004 | Devlin et al. | 524/241 |
| 2004/0119176 A1 | 6/2004 | Xia et al. | 264/1.32 |
| 2004/0120916 A1 | 6/2004 | Huth | 424/70.13 |
| 2004/0120982 A1 | 6/2004 | Diana et al. | 424/420 |
| 2004/0137079 A1 | 7/2004 | Cook et al. | 424/662 |
| 2004/0142829 A1 | 7/2004 | Tsao et al. | 510/112 |
| 2005/0006255 A1 | 1/2005 | Peck | 206/5.1 |
| 2005/0047270 A1 | 3/2005 | Wood et al. | 366/170.3 |
| 2005/0117112 A1 | 6/2005 | Nayiby et al. | 351/160 |
| 2005/0119141 A1 | 6/2005 | Quenville et al. | 510/112 |
| 2005/0154080 A1 | 7/2005 | McCabe et al. | 523/107 |
| 2005/0244509 A1 | 11/2005 | Tsao | 424/616 |
| 2005/0260280 A1 | 11/2005 | Cook et al. | 424/661 |
| 2005/0266089 A1 | 12/2005 | Cook et al. | 424/488 |
| 2006/0063852 A1 | 3/2006 | Iwata et al. | 523/106 |
| 2006/0073185 A1 * | 4/2006 | Jani et al. | 424/427 |
| 2006/0074208 A1 | 4/2006 | Laredo | 526/279 |
| 2006/0094643 A1 | 5/2006 | Svirkin et al. | 514/8 |
| 2006/0135381 A1 | 6/2006 | Hu et al. | 520/112 |
| 2006/0251696 A1 | 11/2006 | Winterton et al. | 424/422 |
| 2007/0010595 A1 | 1/2007 | McCabe et al. | 523/106 |
| 2007/0195261 A1 | 8/2007 | Vogt et al. | 351/158 |

FOREIGN PATENT DOCUMENTS

| | | |
|---|---|---|
| GB | 1340516 | 11/1970 |
| GB | 1340518 | 11/1970 |
| JP | S6452122 A | 2/1989 |
| JP | 2006241085 | 3/2005 |
| JP | 2011006986 | 6/2009 |
| KR | 1994-006102 | 7/1994 |
| WO | WO 94/04028 | 3/1994 |
| WO | WO 94/09794 | 5/1994 |
| WO | WO 95/00615 | 1/1995 |
| WO | WO 95/00618 | 1/1995 |
| WO | WO 95/34327 | 12/1995 |
| WO | WO 97/20019 | 6/1997 |
| WO | 9830248 A2 | 7/1998 |
| WO | WO 00/02937 | 1/2000 |
| WO | WO 00/37048 | 6/2000 |
| WO | WO 01/20997 | 3/2001 |
| WO | WO 01/27174 | 4/2001 |
| WO | WO 01/34312 | 5/2001 |
| WO | WO 01/70837 A1 | 9/2001 |
| WO | WO 02/38161 A1 | 5/2002 |
| WO | WO 2004/055148 A1 | 7/2004 |
| WO | WO 2004/060099 A2 | 7/2004 |
| WO | WO 2004/091438 A2 | 10/2004 |
| WO | WO 2005/011966 A1 | 2/2005 |
| WO | 1857301 A | 4/2005 |
| WO | 2005089715 A1 | 9/2005 |
| WO | WO 2005/092987 A1 | 10/2005 |
| WO | WO2006/009101 A1 | 1/2006 |
| WO | 2006011999 A1 | 2/2006 |
| WO | WO 2006/038080 A2 | 4/2006 |
| WO | WO 2006/061990 A1 | 6/2006 |
| WO | WO 2006/088758 A2 | 8/2006 |
| WO | 2006117228 A2 | 11/2006 |
| WO | 2007098040 A1 | 8/2007 |

OTHER PUBLICATIONS

English Translation of the Office Action, Notification of Reasons for Rejection; Japan Patent Application No. 2014-078104, Dispatch No. 027492, Dispatch Date: Jan. 27, 2015.

Gulsen Derya et al, "Ophthalmic Drug Delivery through Contact Lenses", Investigative Ophthalmology & Visual Science, Jul. 2004, vol. 45, No. 7, pp. 2342-2347.

PCT International Search Report dated Dec. 3, 2009, PCT/US2008/010159.

PCT Written Opinion of the International Searching Authority dated Feb. 28, 2010, PCT/US2008/010159.

* cited by examiner

CONTACT LENS PRODUCTS

This application is a divisional application of application Ser. No. 12/229,769, filed Aug. 27, 2008, which claims the benefits under 35 USC 119 (e) of U.S. provisional application No. 60/969,339 filed Aug. 31, 2007, incorporated by reference in its entirety.

The present invention relates to improved contact lens products which not only have initial insertion comfort but also are comfortable to wear for more than about 6 hours. The present invention also provides methods for making contact lens products of the invention.

BACKGROUND OF THE INVENTION

One long felt need in the contact lens industry is to provide contact lenses which are comfortable for users to wear. Generally, the problems that contact lens users complain of most are initial discomfort (i.e., immediately after lens insertion), discomfort associated with dry-eye conditions and/or working or living in dry environments, and end-of-day comfort. Several approaches have been developed to address the comfort issue.

For example, soft contact lenses have been developed to alleviate some of the problems, such as initial discomfort, relatively long periods of adaptation (a week or two) required for a patient to become accustomed to them, and/or improper fit (lenses become dislodged and/or are very uncomfortable). This is due, not only, to their relatively soft surfaces, but also to their pliability, which permits them to modify their shape somewhat with different eyes.

One of the widely used approaches to improve ocular comfort with contact lenses is to apply directly eye drops of an ocular lubricant into the wearer's eye while the lens is being worn, in order to provide some relief to some extent, e.g., the initial discomfort of wearers, discomfort suffering from dry-eye effects, or end-of-day discomfort. However, there are unavoidable disadvantages with this approach. For example, eye drops are typically applied only after a lens wearer is already suffering discomfort and as such do not prevent the discomfort from occurring. Furthermore, a user needs to easily and conveniently access eye drops to ease the discomfort and therefore has to carry a bottle of eye drops with him/her. This adds cost and inconvenience to the lens wearers.

Recently, surfactants, lubricants or other additives are added in the lens packaging solution to ease to some extent initial discomfort and other symptoms (see, for example, U.S. Pat. Nos. 5,882,687, 5,942,558, 6,348,507, 6,440,366, 6,531, 432, and 6,699,435; and Published PCT Patent Applications WO9720019 and WO2006/088758). However, although such approach may alleviate, to some extent, some forms but not all forms of discomfort, especially the end-of-day comfort, dry-eye symptoms and/or contact lens induced dry-eye symptoms.

In addition, leachable lubricants are incorporated in lens formulations for making contact lenses to alleviate some discomfort symptoms (see for example, U.S. Pat. Nos. 6,822, 016 and 6,367,929, U.S. Patent Application Publication No. US 2006/0251696 A1). Although the methods disclosed in the above patents and patent application may alleviate some discomfort symptoms to some extent, not all symptoms can be removed and/or reduced.

Therefore, there exists a need for hydrogel soft contact lenses which not only have initial insertion comfort but also are comfortable to wear for more than about 6 hours.

SUMMARY OF THE INVENTION

The present invention, in one aspect, provides an ophthalmic product comprising a sealed and sterilized package which include a packaging solution and a soft hydrogel contact lens immersed in the packaging solution, wherein the packaging solution includes a hydroxyl-containing viscosity-enhancing polymer in an amount sufficient to provide the packaging solution a viscosity of from about 1.5 centipoise to about 20 centipoise, preferably from about 2.0 centipoise to about 15 centipoise at 25° C., a polyethylene glycol having a molecular weight of 2000 or less, and one or more buffering agents in an amount sufficient to provide the solution a pH of from about 6.0 to 8.0, wherein the packaging solution has an osmolality of from about 200 to about 450 mOsm/kg. In one preferred embodiment, the hydrogel contact lens comprises a polymer matrix, a first leachable polymeric lubricant, and a second leachable polymeric lubricant, wherein the average molecular weight of the second leachable polymeric lubricant is at least about 3 fold of that of the first leachable polymeric lubricant.

The present invention, in another aspect, provides a process for making a soft contact lens capable of easing wearer's initial discomfort and end-of-day discomfort. The method of the invention comprises the steps of: a) curing a hydrogel lens formulation in a mold to form a hydrogel contact lens, wherein the lens formulation comprises a first leachable polymeric lubricant and a second leachable polymeric lubricant, wherein the first and second leachable polymeric lubricants are incorporated noncovalently and distributed in the matrix of the contact lens, wherein the second leachable polymeric lubricant is different from the first leachable polymeric lubricant in molecular weight or in the polymer composition; b) packaging the hydrogel contact lens in a container containing a packaging solution, wherein the packaging solution comprises a non-ionic viscosity-enhancing polymer in an amount sufficient to provide the packaging solution a viscosity of from about 1.5 centipoise to about 20 centipoise at 25° C., preferably from about 2.0 centipoise to about 15 centipoise at 25° C., and a non-ionic polymeric surfactant having a molecular weight less than about 2,000 daltons; and c) sterilizing the hydrogel contact lens in the package to obtain the soft contact lens.

The present invention, in a further aspect, provides a daily-disposable contact lens, the contact lens comprising a polymer matrix which includes a first leachable polymeric lubricant and a second leachable polymeric lubricant, wherein the second leachable polymeric lubricant has an average molecular weight being at least about 3 fold of the average molecular weight of the first leachable polymeric lubricant.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

"Contact Lens" refers to a structure that can be placed on or within a wearer's eye. A contact lens can correct, improve, or alter a user's eyesight, but that need not be the case. A contact lens can be of any appropriate material known in the art or later developed, and can be a soft lens, a hard lens, or a hybrid lens. A "silicone hydrogel contact lens" refers to a contact lens comprising a silicone hydrogel material.

A "hydrogel" refers to a polymeric material which can absorb at least 10 percent by weight of water when it is fully hydrated. A hydrogel material can be obtained by polymerization or copolymerization of at least one hydrophilic monomer in the presence of or in the absence of additional monomers and/or macromers/prepolymer or by crosslinking of a prepolymer.

A "silicone hydrogel" refers to a hydrogel obtained by copolymerization of a polymerizable composition comprising at least one silicone-containing vinylic monomer or at least one silicone-containing macromer or a silicone-containing prepolymer.

A "monomer" means a low molecular weight compound that can be polymerized actinically or thermally. Low molecular weight typically means average molecular weight less than 700 Daltons. In accordance with the invention, a monomer can be a vinylic monomer or a compound comprising two thiol groups. A compound with two thiol groups can participate in thiol-ene step-growth radical polymerization with a monomer with vinyl group to form a polymer. Step-growth radical polymerization can be used in making contact lenses, as described in a commonly-owned copending U.S. patent application No. 60/869,812 filed Dec. 13, 2006 (entitled "Production of Ophthalmic Devices Based on Photo-Induced Step Growth Polymerization", herein incorporated in reference in its entirety.

A "vinylic monomer", as used herein, refers to a low molecular weight compound that has an ethylenically unsaturated group and can be polymerized actinically or thermally. Low molecular weight typically means average molecular weight less than 700 Daltons.

The term "olefinically unsaturated group" or "ethylentically unsaturated group" is employed herein in a broad sense and is intended to encompass any groups containing at least one $>C=C<$ group. Exemplary ethylenically unsaturated groups include without limitation acryloyl, methacryloyl, allyl, vinyl, styrenyl, or other $C=C$ containing groups.

As used herein, "actinically" in reference to curing or polymerizing of a polymerizable composition or material means that the curing (e.g., crosslinked and/or polymerized) is performed by actinic irradiation, such as, for example, UV irradiation, ionized radiation (e.g. gamma ray or X-ray irradiation), microwave irradiation, and the like. Thermal curing or actinic curing methods are well-known to a person skilled in the art.

The term "fluid" as used herein indicates that a material is capable of flowing like a liquid.

A "hydrophilic monomer" refers to a monomer which can be polymerized actinically or thermally to form a polymer that is water-soluble or can absorb at least 10 percent by weight water.

A "hydrophobic monomer", as used herein, refers to a vinylic monomer which is polymerized actinically or thermally to form a polymer that is insoluble in water and can absorb less than 10 percent by weight water.

A "macromer" refers to a medium and high molecular weight compound which can be polymerized and/or crosslinked actinically or thermally. Medium and high molecular weight typically means average molecular weight greater than 700 Daltons. In accordance with the invention, a macromer comprises one or more ethylenically unsaturated groups and/or one or more thiol groups, which can participate in free radical chain growth polymerization or thiol-ene step-growth radical polymerization. Preferably, a macromer contains ethylenically unsaturated groups and can be polymerized actinically or thermally.

A "prepolymer" refers to a starting polymer which contains crosslinkable groups and can be cured (e.g., crosslinked and/or polymerized) actinically or thermally to obtain a crosslinked and/or polymerized polymer having a molecular weight much higher than the starting polymer. In accordance with the invention, a prepolymer comprises one or more ethylenically unsaturated groups and/or one or more thiol groups, which can participate in free radical chain growth polymerization or thiol-ene step-growth radical polymerization.

A "silicone-containing prepolymer" refers to a prepolymer which contains silicone and can be crosslinked upon actinic radiation or thermally to obtain a crosslinked polymer having a molecular weight much higher than the starting polymer.

"Polymer" means a material formed by polymerizing one or more monomers or macromers or by crosslinking one or more prepolymers.

"Molecular weight" of a polymeric material (including monomeric or macromeric materials), as used herein, refers to the number-average molecular weight unless otherwise specifically noted or unless testing conditions indicate otherwise.

"Visibility tinting" in reference to a lens means dying (or coloring) of a lens to enable the user to easily locate a lens in a clear solution within a lens storage, disinfecting or cleaning container. It is well known in the art that a dye and/or a pigment can be used in the visibility tinting of a lens.

"Dye" means a substance that is soluble in a solvent and that is used to impart color. Dyes are typically translucent and absorb but do not scatter light. Any suitable biocompatible dye can be used in the present invention.

A "pigment" means a powdered substance that is suspended in a liquid in which it is insoluble. A pigment can be a fluorescent pigment, phosphorescent pigment, pearlescent pigment, or conventional pigment. While any suitable pigment may be employed, it is presently preferred that the pigment be heat resistant, non-toxic and insoluble in aqueous solutions.

A "photoinitiator" refers to a chemical that initiates radical crosslinking/polymerizing reaction by the use of light. Suitable photoinitiators include, without limitation, benzoin methyl ether, diethoxyacetophenone, a benzoyl phosphine oxide, 1-hydroxycyclohexyl phenyl ketone, Darocure® types, and Irgacure® types, preferably Darocure® 1173, and Irgacure® 2959.

A "thermal initiator" refers to a chemical that initiates radical crosslinking/polymerizing reaction by the use of heat energy. Examples of suitable thermal initiators include, but are not limited to, 2,2'-azobis(2,4-dimethylpentanenitrile), 2,2'-azobis(2-methylpropanenitrile), 2,2'-azobis(2-methylbutanenitrile), peroxides such as benzoyl peroxide, and the like. Preferably, the thermal initiator is 2,2'-azobis(isobutyronitrile) (AIBN).

An "interpenetrating polymer network (IPN)" as used herein refers broadly to an intimate network of two or more polymers at least one of which is either synthesized and/or crosslinked in the presence of the other(s). Techniques for preparing IPN are known to one skilled in the art. For a general procedure, see U.S. Pat. Nos. 4,536,554, 4,983,702, 5,087,392, and 5,656,210, the contents of which are all incorporated herein by reference. The polymerization is generally carried out at temperatures ranging from about room temperature to about 145° C.

A "spatial limitation of actinic radiation" refers to an act or process in which energy radiation in the form of rays is directed by, for example, a mask or screen or combinations thereof, to impinge, in a spatially restricted manner, onto an area having a well defined peripheral boundary. For example, a spatial limitation of UV radiation can be achieved by using a mask or screen that has a transparent or open region (unmasked region) surrounded by a UV impermeable region (masked region), as schematically illustrated in FIGS. 1-9 of U.S. Pat. No. 6,627,124 (herein incorporated by reference in its entirety). The unmasked region has a well defined peripheral boundary with the unmasked region. The two opposite surfaces (anterior surface and posterior surface) of a resultant contact lens are defined by the two molding surfaces while the edge is defined by the spatial limitation of actinic irradiation rather than by means of mold walls. Typically, only the fluid composition within a region bound by the two molding surfaces and the projection of the well-defined peripheral boundary of the spatial limitation is crosslinked whereas any fluid prepolymer composition outside of and immediately around the peripheral boundary of the spatial limitation is not crosslinked, and thereby the edge of the contact lens should be smooth and precise duplication of the dimension and geometry of the spatial limitation of actinic radiation. The energy used for the crosslinking is radiation energy, especially UV radiation, gamma radiation, electron radiation or thermal radiation, the radiation energy preferably being in the form of a substantially parallel beam in order on the one hand to achieve good restriction and on the other hand efficient use of the energy. Such method of making contact lenses are described in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties.

A "hydrogel lens-forming formulation" or "hydrogel lens-forming material" refers to a polymerizable composition which can be cured (i.e., polymerized and/or crosslinked) thermally or actinically to obtain a crosslinked/polymerized polymeric material. Lens-forming materials are well known to a person skilled in the art. Typically a lens forming material comprises polymerizable/crosslinkable components, for example, such as, monomers, macromers, prepolymers, or combinations thereof, as known to a person skilled in the art. A lens-forming material can further include other components, such as an initiator (e.g., a photoinitiator or a thermal initiator), a visibility tinting agent, UV-blocking agent, photosensitizers, antimicrobial agents (e.g., Ag-nanoparticles), lubricant/wetting agents (e.g., those described above), and the like.

In accordance with the invention, a packaging solution is ophthalmically safe. The term "ophthalmically safe" with respect to a packaging solution is meant that a contact lens immersed in the solution is safe for direct placement on the eye without rinsing, that is, the solution is safe and sufficiently comfortable for daily contact with the eye via a contact lens or carryover to the ocular surface (thus ocular contact) using a contact lens. An ophthalmically safe solution has a tonicity and pH that is compatible with the eye and comprises materials, and amounts thereof, that are not irritating and non-cytotoxic according to international ISO standards and U.S. FDA regulations.

The term "compatible with the eye" means a solution that may be in intimate contact with the eye for an extended period of time without significantly damaging the eye and without significant user discomfort.

A "reduced susceptibility to oxidation degradation of the polyethylene glycol" means that the susceptibility to oxidative degradation of a polyethylene glycol in a solution containing an α-oxo-multi-acid or salt thereof after subject to a sterilization treatment is reduced (characterized by the amount of detectable formic acid and optionally other degradation by-products in a stabilized poly(oxyalkylene)-containing polymeric material being 80% or less, preferably 65% or less, more preferably 50% or less, of that detected in a solution without any α-oxo-multi-acid or salt thereof). The methods for determining formic acid and other by-products derived from oxidative degradation PEG-containing polymeric materials are described in a commonly-owned co-pending patent application (US patent application publication No. 2004/0116564 A1, incorporated herein in its entirety). Alternatively, a person skilled in the art knows how to analyze the oxidative degradation products of a PEG-containing polymeric material.

A "leachable polymeric lubricant" as used herein refer to a hydrophilic polymer which is not covalently bound to but instead is associated with or entrapped in the polymer matrix of a contact lens and which can enhance surface wettability of a contact lens and/or the eye or reduce the frictional character of the contact lens surface.

The present invention is generally directed to a hydrogel contact lens capable of easing lens-wearer's initial discomfort and providing wearer a comfort for a prolonged time period, more than six hours. The present invention is partly based on the discovery that, by packaging and storing a hydrogel lens with two or more leachable polymeric lubricants incorporated therein in a relatively viscous packaging solution including a relatively low molecular weight polyethylene glycol (PEG) and a viscosity-enhancing hydrophilic polymer (e.g., polyvinylalcohol (PVA) or hydroxypropylmethyl cellulose (HPMC) or similar hydroxyl-containing polymers), most discomfort problems associated currently available contact lenses can be alleviated.

Although the inventors do not wish to be bound by any particular theory, it is believed that a low molecular weight PEG and HPMC (or PVA or a high molecular weight nonionic hydrophilic polymer having hydroxyl groups) can have a synergetic effects on the initial comfort (at the time of inserting the lens) and during a first several hours of lens wearing. By immersing a hydrogel lens in a relatively viscous lens packaging solution, a viscous film, which is believed to be composed of HPMC (or PVA or a high molecular weight nonionic hydrophilic polymer having hydroxyl groups) and low molecular weight PEG, may be formed temporally on the surface of the lens which can be served as a cushion to ease in particular initial discomfort and may also function as both as a barrier to the leachable polymeric lubricant tending releasing into the lens packaging solution and a temporary reservoir for the leachable polymeric lubricant capable of providing a release burst of leachable polymeric lubricant into the ocular environment of the eye. The low molecular weight PEG together with HPMC (or PVA or a high molecular weight nonionic hydrophilic polymer having hydroxyl groups) can lower the surface tension and the friction of the viscous film of the lens surface, thereby increasing the wear's comfort.

It is also believed that when the average molecular weight of two or more polymeric lubricants are different from each other to an extent so large, their release may occur at a different time scale: the lubricant with low molecular weight releasing first and the lubricant with higher molecular weight releasing later. By having at least about 3 fold difference in molecular weight between two lubricants, one can ensure that the higher molecular weight lubricant would release into the eye after about 6 hours of wearing time. A hydrogel contact lens of the invention may provide prolonged wearer comfort and in particular end-of-day comfort even after stored in a packaging solution for an extended period of time, e.g., up to about 5 years.

The present invention, in one aspect, provides an ophthalmic product comprising a sealed and sterilized package which include a packaging solution and a soft hydrogel contact lens immersed in the packaging solution, wherein the packaging solution includes a hydroxyl-containing viscosity-enhancing polymer in an amount sufficient to provide the packaging solution a viscosity of about 1.5 centipoise to about 20 centipoise at 25° C., a polyethylene glycol having a molecular weight of 2000 or less, and one or more buffering agents in an amount sufficient to provide the solution a pH of from about 6.0 to 8.0, wherein the packaging solution has an osmolality of from about 200 to about 450 mOsm/kg. In one preferred embodiment, the hydrogel contact lens comprises a polymer matrix, a first leachable polymeric lubricant, and a second leachable polymeric lubricant, wherein the second leachable polymeric lubricant is different from the first leachable polymeric lubricant in molecular weight or in the polymer composition (i.e., made of different monomer units or same monomer units but different percentage).

Lens packages (or containers) are well known to a person skilled in the art for autoclaving and storing a soft contact lens. Any lens package can be used in the invention. Preferably, a lens package is a blister package which comprises a base and a cover, wherein the cover is detachably sealed to the base, wherein the base includes a cavity for receiving a sterile packaging solution and the contact lens.

Lenses are packaged in individual packages, sealed, and sterilized (e.g., by autoclave) prior to dispensing to users. A person skilled in the art will understand well how to seal and sterilize lens packages.

In accordance with the invention, a soft hydrogel contact lens can be a conventional hydrogel contact lens (i.e., a non-silicone hydrogel lens) or a silicone hydrogel contact lens.

A packaging solution of the invention is ophthalmically compatible and may be any water-based solution that is used for the storage of contact lenses. A packaging solution of the invention can be a saline solution, a buffered solution, and deionized water.

The solution of the invention contains a hydroxyl-containing viscosity-enhancing polymer. The viscosity-enhancing polymer preferably is nonionic. Increasing the solution viscosity provides a film on the lens which may facilitate comfortable wearing of the contact lens. The viscosity-enhancing component may also act to cushion the impact on the eye surface during insertion and serves also to alleviate eye irritation.

Preferred viscosity-enhancing polymers include, but are not limited to, water soluble cellulose-derived polymers, water-soluble polyvinylalcohols (PVAs), high molecular weight poly(ethylene oxide) having a molecular weight greater than about 2000 (up to 10,000,000 daltons), a copolymer of at least one vinyl lactam with one or more hydroxyl-containing monomers, and the like. Water soluble cellulose-derived polymers are most preferred viscosity-enhancing polymers. Examples of useful cellulose-derived polymers include without limitation cellulose ethers.

Exemplary preferred cellulose ethers are methyl cellulose (MC), ethyl cellulose, hydroxymethylcellulose, hydroxyethyl cellulose (HEC), hydroxypropylcellulose (HPC), hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of from about 0.01% to about 5% by weight, preferably from about 0.05% to about 3% by weight, even more preferably from about 0.1% to about 1% by weight, based on the total amount of the packaging solution.

It is understood that other viscosity-enhancing polymers, such as polyvinylpyrrolidone polymer including copolymers, can be optionally added in the solution.

A packaging solution of the invention has a viscosity of from 1.5 centipoise to about 20 centipoise at 25° C., preferably from about 2.0 centipoise to about 15 centipoise at 25° C., more preferably from about 2.0 centipoise to about 8 centipoise at 25° C.

In accordance with the invention, the packaging solution comprises a polyethylene glycol having a molecular weight of 2000 or less, preferably 1000 or less, even more preferably 600 or less, most preferably from about 100 to about 500 daltons.

In a preferred embodiment of the invention, the packaging solution comprises an α-oxo-multi-acid or salt thereof in an amount sufficient to have a reduced susceptibility to oxidation degradation of the polyethylene glycol in the packaging solution. A commonly-owned co-pending patent application (US patent application publication No. 2004/0116564 A1, incorporated herein in its entirety) discloses that oxo-multi-acid or salt thereof can reduce the susceptibility to oxidative degradation of a PEG-containing polymeric material.

Exemplary α-oxo-multi-acids or biocompatible salts thereof include without limitation citric acid, 2-ketoglutaric acid, or malic acid or biocompatible (preferably ophthalmically compatible) salts thereof. More preferably, an α-oxo-multi-acid is citric or malic acid or biocompatible (preferably ophthalmically compatible) salts thereof (e.g., sodium, potassium, or the like).

The solution of the present invention preferably contains a buffering agent. The buffering agents maintain the pH preferably in the desired range, for example, in a physiologically acceptable range of about 6 to about 8. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (2-amino-2-hydroxymethyl-1,3-propanediol), Bis-Tris(Bis-(2-hydroxyethyl)-imino-tris-(hydroxymethyl)-methane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS (3-[N-morpholino]-propanesulfonic acid), PIPES (piperazine-N,N'-bis(2-ethanesulfonic acid), TES (N-[Tris(hydroxymethyl)methyl]-2-aminoethanesulfonic acid), salts thereof, phosphate buffers, e.g. $Na_2HPO_4$, $NaH_2PO_4$, and $KH_2PO_4$ or mixtures thereof. A preferred bis-aminopolyol is 1,3-bis(tris[hydroxymethyl]-methylamino)propane (bis-TRIS-propane). The amount of each buffer agent is that amount necessary to be effective in achieving a pH of the composition of from about 6.0 to about 8.0. Typically, it is present in an amount of from 0.001% to 2%, preferably from 0.01% to 1%; most preferably from about 0.05% to about 0.30% by weight.

The solutions according to the invention are preferably formulated in such a way that they are isotonic with the lacrimal fluid. A solution which is isotonic with the lacrimal fluid is generally understood to be a solution whose concentration corresponds to the concentration of a 0.9% sodium chloride solution (308 mOsm/kg). Deviations from this concentration are possible throughout; if desired.

The isotonicity with the lacrimal fluid, or even another desired tonicity, may be adjusted by adding organic or inorganic substances which affect the tonicity. Suitable occularly acceptable tonicity agents include, but are not limited to sodium chloride, potassium chloride, glycerol, propylene glycol, polyols, mannitols, sorbitol, xylitol and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

In accordance with the invention, the solution can further comprises mucin-like materials, ophthalmically beneficial materials, and/or surfactants.

Exemplary mucin-like materials include without limitation polyglycolic acid, polylactides, and the likes. A mucin-like material can be used as guest materials which can be released continuously and slowly over extended period of time to the ocular surface of the eye for treating dry eye syndrome. The mucin-like material preferably is present in effective amounts.

Exemplary ophthalmically beneficial materials include without limitation 2-pyrrolidone-5-carboxylic acid (PCA), amino acids (e.g., taurine, glycine, etc.), alpha hydroxyl acids (e.g., glycolic, lactic, malic, tartaric, mandelic and citric acids and salts thereof, etc.), linoleic and gamma linoleic acids, and vitamins (e.g., B5, A, B6, etc.).

Surfactants can be virtually any occularly acceptable surfactant including non-ionic, anionic, and amphoteric surfactants. Examples of preferred surfactants include without limitation poloxamers (e.g., Pluronic® F108, F88, F68, F68LF, F127, F87, F77, P85, P75, P104, and P84), poloamines (e.g., Tetronic® 707, 1107 and 1307, polyethylene glycol esters of fatty acids (e.g., Tween® 20, Tween® 80), polyoxyethylene or polyoxypropylene ethers of $C_{12}$-$C_{18}$ alkanes (e.g., Brij® 35), polyoxyethyene stearate (Myrj® 52), polyoxyethylene propylene glycol stearate (Atlas® G 2612), and amphoteric surfactants under the trade names Mirataine® and Miranol®.

In one preferred embodiment, the hydrogel contact lens comprises a polymer matrix, a first leachable polymeric lubricant, and a second leachable polymeric lubricant, wherein the second leachable polymeric lubricant is different from the first leachable polymeric lubricant in molecular weight or in the polymer composition. More preferably, the average molecular weight of the second leachable polymeric lubricant is at least about 3 fold of that of the first leachable polymeric lubricant.

The lens can be prepared according to any methods known to a person skilled in the art from a hydrogel lens-forming formulation including two or more non-crosslinkable hydrophilic polymers (i.e., leachable polymeric lubricants) with different molecular weights.

In accordance with the present invention, a hydrogel lens-forming formulation (or a polymerizable fluid composition) can be a solution or a solvent-free liquid or melt at a temperature below 60° C.

Where a polymerizable fluid composition is a solution, it can be prepared by dissolving at least one polymerizable/crosslinkable component (e.g., one or more monomers, one or more macromers and/or one or more prepolymers) and all other desired components in any suitable solvent known to a person skilled in the art. Examples of suitable solvents are water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acetone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

In accordance with the present invention, a polymerizable fluid composition comprises at least two different and non-crosslinkable hydrophilic polymers and at least one actinically-crosslinkable prepolymer. It can be a solution, a solvent-free liquid, or a melt and comprises an actinically-crosslinkable prepolymer. Preferably, a fluid composition is a solution of at least one actinically prepolymer. More preferably, a fluid composition is an aqueous solution of at least one actinically-crosslinkable prepolymer. It is understood that a fluid composition can also (but preferably does not) comprise one or more monomers, one or more macromers, and/or one or more crosslinking agents. However, the amount of those components should be so small that a hydrogel lens made from the fluid composition does not contain unacceptable levels of unpolymerized monomers, macromers and/or crosslinking agents. The presence of unacceptable levels of unpolymerized monomers, macromers and/or crosslinking agents may require extraction to remove them. Similarly, a fluid composition can further comprise various components, such as polymerization initiators (e.g., photoinitiator or thermal initiator), photosensitizers, inhibitors, fillers, and the like, so long their presence in a lens does not require the lens to be subjected any extraction treatment.

Examples of suitable photoinitiators are benzoin methyl ether, 1-hydroxycyclohexyl-phenyl ketone, or Darocure® or Irgacure® types, for example Darocure® 1173 or Irgacure® 2959. The amount of photoinitiator may be selected within wide limits, an amount of up to 0.05 g/g of prepolymer and especially of up to 0.003 g/g of prepolymer having proved beneficial. A person skilled in the art will know well how to select a photoinitiator.

The solution of the prepolymer and the leachable lubricants defined hereinbefore is preferably a pure solution which means a solution which is free or essentially free from undesired constituents, for example, free from monomeric, oligomeric or polymeric starting compounds used for the preparation of the prepolymer, and/or free from secondary products formed during the preparation of the prepolymer.

A further solvent of the aqueous prepolymer solution may be, for example an alcohol, such as methanol, ethanol or n- or iso-propanol, or a carboxylic acid amide, such as N,N-dimethylformamide, or dimethyl sulfoxide. The aqueous solution preferably contains no further solvent.

The aqueous solution of the prepolymer preferably does not contain a comonomer that needs to be removed after the lens is formed.

A preferred group of prepolymers are those which are soluble in water, a water-organic solvent mixture and an organic solvent, meltable at a temperature below about 85° C., and are ophthalmically compatible. It would be advantageous that an actinically-crosslinkable prepolymer are in a substantially pure form (e.g., purified by ultrafiltration to remove most reactants for forming the prepolymer). Therefore, after crosslinking by actinic radiation, a medical device, preferably an ophthalmic device may require practically no more subsequent purification, such as in particular complicated extraction of unpolymerized constituents. Furthermore, crosslinking may take place solvent-free or in aqueous solution, so that a subsequent solvent exchange or the hydration step is not necessary.

Examples of preferred actinically crosslinkable prepolymers include, but are not limited to, a water-soluble crosslinkable poly(vinyl alcohol) prepolymer described in U.S. Pat. Nos. 5,583,163 and 6,303,687 (incorporated by reference in their entireties); a water-soluble vinyl group-terminated polyurethane prepolymer described in U.S. Patent Application Publication No. 2004/0082680 (herein incorporated by reference in its entirety); derivatives of a polyvinyl alcohol, polyethyleneimine or polyvinylamine, which are disclosed in U.S. Pat. No. 5,849,841 (incorporated by reference in its entirety); a water-soluble crosslinkable polyurea prepolymer described in U.S. Pat. No. 6,479,587 and in commonly owned pending U.S. patent application Ser. No. 10/991,124 filed on Nov. 17, 2004 (herein incorporated by reference in their entireties); crosslinkable polyacrylamide; crosslinkable statistical copolymers of vinyl lactam, MMA and a comonomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635 and U.S. Pat. No. 6,492,478; branched polyalkylene glycolurethane prepolymers disclosed in EP 958,315 and U.S. Pat. No. 6,165,408; polyalkylene glycol-tetra(meth)acrylate prepolymers disclosed in EP 961,941 and U.S. Pat. No. 6,221,303; and crosslinkable polyallylamine gluconolactone prepolymers disclosed in PCT patent application WO 2000/31150 and U.S. Pat. No. 6,472,489.

Examples of silicone-containing prepolymers are those described in commonly-owned US Published Patent Application No. US 2001-0037001 A1 and U.S. Pat. No. 6,039,913, which are incorporated herein by references in their entireties.

In a preferred embodiment, an actinically-crosslinkable prepolymer is a water-soluble crosslinkable poly(vinyl alcohol).

In another preferred embodiment, an actinically-crosslinkable prepolymer is a crosslinkable polyurea as described in U.S. Pat. No. 6,479,587 or in a commonly assigned copending U.S. patent application Ser. No. 10/991,124 filed on Nov. 17, 2004 (herein incorporated by reference in their entireties).

In accordance with the invention, the criterion that the prepolymer is soluble in water denotes in particular that the prepolymer is soluble in a concentration of approximately from 3 to 90% by weight, preferably approximately from 5 to 60% by weight, especially approximately from 10 to 60% by weight, in a substantially aqueous solution. Insofar as it is possible in an individual case, prepolymer concentrations of more than 90% are also included in accordance with the invention. Especially preferred concentrations of the prepolymer in solution are from approximately 15 to approximately 50% by weight, especially from approximately 15 to approximately 40% by weight, for example from approximately 25% to approximately 40% by weight.

Preferably, the prepolymers used in the process according to the invention are previously purified in a manner known per se, for example by precipitation with organic solvents, such as acetone, filtration and washing, extraction in a suitable solvent, dialysis or ultrafiltration, ultrafiltration being especially preferred. By means of that purification process the prepolymers can be obtained in extremely pure form, for example in the form of concentrated aqueous solutions that are free, or at least substantially free, from reaction products, such as salts, and from starting materials, such as, for example, non-polymeric constituents.

The preferred purification process for the prepolymers used in the process according to the invention, ultrafiltration, can be carried out in a manner known per se. It is possible for the ultrafiltration to be carried out repeatedly, for example from two to ten times. Alternatively, the ultrafiltration can be carried out continuously until the selected degree of purity is attained. The selected degree of purity can in principle be as high as desired. A suitable measure for the degree of purity is, for example, the concentration of dissolved salts obtained as by-products, which can be determined simply in known manner.

In accordance with the invention, leachable lubricants are non-crosslinkable hydrophilic polymers (i.e. without actinically-crosslinkable groups) preferably having no charges. Any suitable hydrophilic polymers can be used so long as they are compatible with the lens-forming material (i.e., can produce optically clear contact lenses). Exemplary non-crosslinkable (i.e. without actinically-crosslinkable groups) hydrophilic polymers include, but are not limited to, polyvinyl alcohols (PVAs), polyamides, polyimides, polylactone, a homopolymer of a vinyl lactam, a copolymer of at least one vinyl lactam in the presence or in the absence of one or more hydrophilic vinylic comonomers, alkylated polyvinylpyrrolidones, a homopolymer of acrylamide or methacrylamide, a copolymer of acrylamide or methacrylamide with one or more hydrophilic vinylic monomers, poly(ethylene oxide) (PEO), a polyoxyethylene derivative, poly-N—N-dimethylacrylamide, polyacrylic acid, poly 2 ethyl oxazoline, heparin polysaccharides, polysaccharides, and mixtures thereof.

Examples of N-vinyl lactams include N-vinyl-2-pyrrolidone, N-vinyl-2-piperidone, N-vinyl-2-caprolactam, N-vinyl-3-methyl-2-pyrrolidone, N-vinyl-3-methyl-2-piperidone, N-vinyl-3-methyl-2-caprolactam, N-vinyl-4-methyl-2-pyrrolidone, N-vinyl-4-methyl-2-caprolactam, N-vinyl-5-methyl-2-pyrrolidone, N-vinyl-5-methyl-2-piperidone, N-vinyl-5,5-dimethyl-2-pyrrolidone, N-vinyl-3,3,5-trimethyl-2-pyrrolidone, N-vinyl-5-methyl-5-ethyl-2-pyrrolidone, N-vinyl-3,4,5-trimethyl-3-ethyl-2-pyrrolidone, N-vinyl-6-methyl-2-piperidone, N-vinyl-6-ethyl-2-piperidone, N-vinyl-3,5-dimethyl-2-piperidone, N-vinyl-4,4-dimethyl-2-piperidone, N-vinyl-7-methyl-2-caprolactam, N-vinyl-7-ethyl-2-caprolactam, N-vinyl-3,5-dimethyl-2-caprolactam, N-vinyl-4,6-dimethyl-2-caprolactam, and N-vinyl-3,5,7-trimethyl-2-caprolactam.

The number-average molecular weight $M_n$ of the hydrophilic polymer is preferably from 10,000 to 500,000, more preferably from 20,000 to 200,000.

Examples of polyvinylpyrrolidone (PVP) include without limitation those polymer characterized by molecular weight grades of K-15, K-30, K-60, K-90, K-120, and the likes.

Examples of copolymers of n-vinylpyrrolidone with one ore more vinylic monomers includes without limitation vinylpyrrolidone/vinylacetate copolymers, vinylpyrrolidone/dimethylaminoethylmethacrylate copolymers (e.g., Copolymer 845, Copolymer 937, Copolymer 958 from ISP Corporation), vinylpyrrolidone/vinylcaprolactam/dimethylaminoethylmethacrylate copolymer.

Examples of alkylated pyrrolidones includes without limitation the family of GANEX® Alkylated pyrrolidone from ISP Corporation.

A suitable polyoxyethylene derivative is, for example, n-alkylphenyl polyoxyethylene ether, n-alkyl polyoxy-ethylene ether (e.g., TRITON®), polyglycol ether surfactant (TERGITOL®), polyoxyethylenesorbitan (e.g., TWEEN®), polyoxyethylated glycol monoether (e.g., BRIJ®, polyoxylethylene 9 lauryl ether, polyoxylethylene 10 ether, polyoxylethylene 10 tridecyl ether), or a block copolymer of ethylene oxide and propylene oxide.

Examples of block copolymers of ethylene oxide and propylene oxide include without limitation poloxamers and poloxamines, which are available, for example, under the tradename PLURONIC®, PLURONIC-R®, TETRONIC®, TETRONIC-R® or PLURADOT®. Poloxamers are triblock copolymers with the structure PEO-PPO-PEO (where "PEO" is poly(ethylene oxide) and "PPO" is poly(propylene oxide).

A considerable number of poloxamers is known, differing merely in the molecular weight and in the PEO/PPO ratio; Examples of poloxamers include 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407. The order of polyoxyethylene and polyoxypropylene blocks can be reversed creating block copolymers with the structure PPO-PEO-PPO, which are known as PLURONIC-R® polymers.

Poloxamines are polymers with the structure (PEO-PPO)$_2$-N—(CH$_2$)$_2$—N-(PPO-PEO)$_2$ that are available with different molecular weight and PEO/PPO ratios. Again, the order of polyoxyethylene and polyoxypropylene blocks can be reversed creating block copolymers with the structure (PPO-PEO)$_2$-N—(CH$_2$)$_2$—N-(PEO-PPO)$_2$, which are known as TETRONIC-R® polymers.

Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available under the tradename PLURADOT®.

Non-crosslinkable PVAs of all kinds, for example those with low, medium or high polyvinyl acetate contents may be employed. In addition, the PVAs used may also comprise small proportions, for example up to 20%, preferably up to 16%, of copolymer units as mentioned before. The use of non-reactive PVAs with a contents of polyvinyl acetate units of less than 20%, preferably lower than 16%, is preferred.

The non-crosslinkable polyvinyl alcohols employed in the present invention are known and are commercially available, for example under the brand name Mowiol® from KSE (Kuraray Specialties Europe) or Gohsenol (Nippon Gohsei, Japan).

It is understood that the addition of the leachable lubricants into the lens formulation should not affect adversely the optical transparency of the result lenses. The leachable lubricants can be the same polymers having different molecular weight or different polymers having different molecular weight.

The present invention, in another aspect, provides a process for making a soft contact lens capable of easing wearer's initial discomfort and end-of-day discomfort. The method of the invention comprises the steps of: a) curing a hydrogel lens formulation in a mold to form a hydrogel contact lens, wherein the lens formulation comprises a first leachable polymeric lubricant and a second leachable polymeric lubricant, wherein the first and second leachable polymeric lubricants are incorporated noncovalently and distributed in the matrix of the contact lens, wherein the second leachable polymeric lubricant is different from the first leachable polymeric lubricant in molecular weight or in the polymer composition; b) packaging the hydrogel contact lens in a container containing a packaging solution, wherein the packaging solution comprises a viscosity-enhancing polymer in an amount sufficient to provide the packaging solution a viscosity of from about 1.5 centipoise to about 20 centipoise at 25° C., preferably from about 2.0 centipoise to about 15 centipoise at 25° C., and a polymeric surfactant having a molecular weight less than about 2,000 daltons; and c) sterilizing the hydrogel contact lens in the package to obtain the soft contact lens.

Above described various embodiments and preferred embodiments of packaging solutions, viscosity-enhancing polymers, the viscosities of the packaging solution, hydrogel lens-forming formulations (lens-forming materials), leachable lubricants, packages, sealing and sterilization, and the others can be used in this aspect of the invention.

Lens molds for making contact lenses are well known to a person skilled in the art and, for example, are employed in cast molding or spin casting. For example, a mold (for full cast molding) generally comprises at least two mold sections (or portions) or mold halves, i.e. first and second mold halves. The first mold half defines a first molding (or optical) surface and the second mold half defines a second molding (or optical) surface. The first and second mold halves are configured to receive each other such that a lens forming cavity is formed between the first molding surface and the second molding surface. The molding surface of a mold half is the cavity-forming surface of the mold and in direct contact with a fluid polymerizable composition.

Methods of manufacturing mold sections for cast-molding a contact lens are generally well known to those of ordinary skill in the art. Virtually all materials known in the art for making molds can be used to make molds for making contact lenses. For example, polymeric materials, such as polyethylene, polypropylene, polystyrene, PMMA, a cyclic olefin copolymer, such as for example, Topas® COC grade 8007-S10 (clear amorphous copolymer of ethylene and norbornene) from Ticona GmbH of Frankfurt, Germany and Summit, N.J., Zeonex® and Zeonor® from Zeon Chemicals LP, Louisville, Ky., or the like can be used. Other materials that allow UV light transmission could be used, such as quartz glass and sapphire.

A person skilled in the art will know well how to cast mold lenses from a lens-forming formulation in molds based on thermal or actinic polymerization.

In a preferred embodiment, when the polymerizable components in the fluid composition is composed essentially of prepolymers, reusable molds are used and the fluid composition is cured actinically under a spatial limitation of actinic radiation to form a colored contact lens. Examples of preferred reusable molds are those disclosed in U.S. patent application Ser. No. 08/274,942 filed Jul. 14, 1994, Ser. No. 10/732,566 filed Dec. 10, 2003, Ser. No. 10/721,913 filed Nov. 25, 2003, and U.S. Pat. No. 6,627,124, which are incorporated by reference in their entireties.

Opening of the mold so that the molded lens can be removed from the mold may take place in a manner known per se.

If the molded contact lens is produced solvent-free from an already purified prepolymer according to the invention, then after removal of the molded lens, it is not normally necessary to follow up with purification steps such as extraction. This is because the prepolymers employed do not contain any undesired constituents of low molecular weight; consequently, the crosslinked product is also free or substantially free from such constituents and subsequent extraction can be dispensed with. Accordingly, the contact lens can be directly transformed in the usual way, by hydration in a packaging solution of the invention (described above), into a ready-to-use contact lens.

If the molded contact lens is produced from an aqueous solution of an already purified prepolymer according to the invention, then the crosslinked product also does not contain any troublesome impurities. It is therefore not necessary to carry out subsequent extraction. Since crosslinking is carried out in an essentially aqueous solution, it is additionally unnecessary to carry out subsequent hydration.

Contact lenses can be sterilized by autoclaving them in a manner known per se after their removal from the molds.

The present invention, in a further aspect, provides a daily-disposable contact lens, the contact lens comprising a polymer matrix which includes a first leachable polymeric lubricant and a second leachable polymeric lubricant, wherein the second leachable polymeric lubricant has an average molecular weight being at least about 3 fold of the average molecular weight of the first leachable polymeric lubricant.

Above described various embodiments and preferred embodiments of hydrogel lens-forming formulations (lens-forming materials), leachable lubricants, and the others can be used in this aspect of the invention.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Lens Formulations

Fluid prepolymer compositions (aqueous formulations) are prepared from nelfilcon A (an acrylated-poly(vinyl alcohol) which is water-soluble and actinically-crosslinkable, from CIBA Vision), water, photoinitiator (Irgacure 2959; Ciba Specialty Chemicals), poloxamer 108 (Pluronic® F38), and GH-22 from Gohsenol and copper phthalocyanine (CuP).
Formulation I.

Formulation I is prepared to contain 30.6% by weight of nelfilcon A, 0.095% of Irgacure 2959 (by weight measured as percentage of total macromer solid), 0.3% by weight of poloxamer 108, 0.5% of Mowiol 6-98 (non-crosslinkable PVA; by weight measured as percentage of total macromer solid) and 1.5% of Gohsenol GH-22 (by weight measured as percentage of total macromer solid), and CuP in an amount to provide the formulation a transmittance of 97%.
Formulation II.

Formulation II is prepared to contain 30.6% by weight of nelfilcon A, 0.095% of Irgacure 2950, 0.3% of poloxamer 108, 1.5% of Mowiol 6-98, and 0.5% of Mowiol 10-98 (by weight measured as percentage of total macromer solid), and CuP in an amount to provide the formulation a transmittance of 98%.
Lens Production Formulations prepared in above are dispensed onto a female mold half by using an EFD automatic dispenser (4 bar, 1.2 sec). The female mold half is then mated with a corresponding male mold half. The mold is closed by using a pneumatic closing system. The formulation is UV cured under 2 different UV lights (1.8 mW/cm$^2$ each) for total exposure time of 4.9 sec.

Each lens is packaged in a conventional blister package containing the corresponding packaging solution and sealed with an aluminum sealing foil. Each lens is then autoclaved in the package. After autoclaving, the diameter and the E-modulus of the contact lenses are determined. No significant differences in mechanical properties (modulus, elongation, stress, and toughness at break) can be identified between lenses made from the control formulation and formulations I and II. The diameters of lenses made from formulation I or II are slightly larger than lenses made from formulation without addition of non-crosslinkable PVAs.

EXAMPLE 2

Lens Packaging Salines

A series of packaging salines containing 1.0% polyethylene glycol (PEG400), 0.294% sodium citrate dihydrate, 0.3297% sodium chloride, 0.8105% disodium hydrogen phosphate dihydrate, 0.0034% poloxamer 108, and water are prepared with varying concentrations (w/w) of HPMC (0.1%, 0.15%, 0.2%, 0.3%, 0.4%). Lenses from Example 1 (formulation I) are packaged in the different salines and autoclaved. The viscosity of the packaging saline in the finished lens blisters (packages) is then measured for each test saline.

| | HPMC (wt %) | | | | | | | | |
|---|---|---|---|---|---|---|---|---|---|
| | 0 | 0.05 | 0.10 | 0.15 | 0.20 | 0.30 | 0.40 | 0.50 | 0.60 |
| Viscosity (cp) | 0.9 | 1.4 | 1.9 | 2.4 | 3.8 | 5.7 | 11.9 | 16.0 | 22.7 |

EXAMPLE 3

Lens Packaging Solutions

Packaging Solution I.
Solution I is prepared to contain 0.15% by weight of HPMC, 1.0% polyethylene glycol (PEG400), 0.294% sodium citrate dihydrate, 0.3297% sodium chloride, 0.8105% disodium hydrogen phosphate dihydrate, 0.0034% poloxamer 108, and water.
Packaging Solution II.
Solution II is prepared to contain 0.4395% sodium chloride, 1.0806% disodium hydrogen phosphate dehydrate, 0.0045% poloxamer 108, and water.

EXAMPLE 4

Lens Production

Lenses produced as in Example 1 (formulation I) are packaged in packaging solution I from Example 3. Lenses produced as in Example I (formulation II) are packaged in packaging solution II from Example 3. The lenses are then autoclaved.

EXAMPLE 5

The release of moisturizing agents from the lenses in Example 4 is monitored following the procedure of Winterton et al., *J of Biomed Mater Res Part B: Appl Biomater* 80B:

424-432, 2007 with the exception that the lenses are gently blotted to remove the packaging saline prior to testing instead of rinsing them briefly in PBS. HPLC analysis revealed PEG-400 elution from the lenses for up to two hours.

EXAMPLE 6

Clinical evaluation of the lenses from Example 4 shows a strong patient preference for lenses made from formulation 1 and packaged in packaging solution I compared to lenses made from formulation II and packaged in packaging solution II.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

The invention claimed is:

1. A process for making a soft contact lens, comprising the steps of:
a) curing a hydrogel lens-forming formulation in a mold to form a hydrogel contact lens, wherein the lens formulation comprises a first leachable polymeric lubricant and a second leachable polymeric lubricant, wherein the first and second leachable polymeric lubricants are incorporated noncovalently and distributed in the matrix of the contact lens, wherein the number-average molecular weight of the second leachable polymeric lubricant is at least 3 folds of the number-average molecular weight of the first leachable polymeric lubricant;
b) packaging the hydrogel contact lens in a container containing a relative-viscous packaging solution having a viscosity of from 2.0 centipoise to 8 centipoise at 25° C., wherein the relative-viscous packaging solution comprises (1) from 0.1% to 1% by weight of a hydroxyl-containing viscosity-enhancing polymer selected from the group consisting of hydroxymethylcellulose, hydroxyethyl cellulose, hydroxypropylcellulose, hydroxypropylmethyl cellulose, and a mixture thereof, (2) a polyethylene glycol having a molecular weight of 2000 or less, (3) an α-oxo-multi-acid or salt thereof in an amount sufficient to have a reduced susceptibility to oxidation degradation of the polyethylene glycol in the relative-viscous packaging solution, and (4) one or more buffering agents in an amount sufficient to provide the solution a pH of from 6.0 to 8.0, wherein the packaging solution has an osmolality of from 200 to 450 mOsm/kg; and
c) sterilizing the hydrogel contact lens immersed in the relatively-viscous packaging solution in the package to obtain the soft contact lens that is characterized by its capability of easing lens-wearer's initial discomfort and providing a wearer with a comfort for a prolonged time period of more than six hours.

2. The process of claim 1, wherein the α-oxo-multi-acid is selected from the group consisting of citric acid, 2-ketoglutaric acid, and malic acid.

3. The process of claim 2, wherein the α-oxo-multi-acid is citric acid.

4. The process of claim 1, wherein the viscosity-enhancing polymer is hydroxypropylmethyl cellulose.

5. The process of claim 1, wherein the polyethylene glycol has a molecular weight of 600 daltons.

6. The process of claim 1, wherein the hydrogel lens-forming formulation comprises at least one actinically-crosslinkable prepolymer which is soluble in water, a water-organic solvent mixture or an organic solvent, or meltable at a temperature below 85° C.

7. The process of claim 6, wherein the actinically-crosslinkable prepolymer is selected from the group consisting of a water-soluble crosslinkable poly(vinyl alcohol) prepolymer; a water-soluble vinyl group-terminated polyurethane prepolymer; derivatives of a polyvinyl alcohol, derivatives of a polyethyleneimine, derivatives of a polyvinylamine; a water-soluble crosslinkable polyurea prepolymer; crosslinkable polyacrylamide; crosslinkable statistical copolymers of vinyl lactam, MMA and a comonomer; crosslinkable copolymers of vinyl lactam, vinyl acetate and vinyl alcohol; polyether-polyester copolymers with crosslinkable side chains; branched polyalkylene glycol-urethane prepolymers; polyalkylene glycol-tetra(meth)acrylate prepolymers; and crosslinkable polyallylamine gluconolactone prepolymers, and mixtures thereof.

8. The process of claim 1, wherein the first and second leachable lubricants, independently of each other, are non-crosslinkable and non-charged hydrophilic polymers selected from the group consisting of polyvinyl alcohols, polyamides, polyimides, polylactone, homopolymers of a vinyl lactam, copolymers of at least one vinyl lactam and at least one hydrophilic vinylic monomer, alkylated polyvinylpyrrolidones, homopolymers of acrylamide, homopolymers of methacrylamide, copolymers of acrylamide and at least one hydrophilic vinylic monomer, copolymers of methacrylamide with at least one hydrophilic vinylic monomer, polyethylene oxide, a polyoxyethylene derivative, poly-N—N-dimethylacrylamide, poly 2 ethyl oxazoline, heparin polysaccharides, polysaccharides, and mixtures thereof.

9. The process of claim 3, wherein the viscosity-enhancing polymer is hydroxypropylmethyl cellulose.

10. The process of claim 9, wherein the polyethylene glycol has a molecular weight of 600 daltons.

11. The process of claim 10, wherein the hydrogel lens-forming formulation comprises at least one actinically-crosslinkable prepolymer which are soluble in water, a water-organic solvent mixture or an organic solvent, or meltable at a temperature below about 85° C., wherein the actinically-crosslinkable prepolymer is selected from the group consisting of a water-soluble crosslinkable poly(vinyl alcohol) prepolymer; a water-soluble vinyl group-terminated polyurethane prepolymer; derivatives of a polyvinyl alcohol, derivatives of a polyethyleneimine, derivatives of a polyvinylamine; a water-soluble crosslinkable polyurea prepolymer; crosslinkable polyacrylamide; crosslinkable statistical copolymers of vinyl lactam, MMA and a comonomer; crosslinkable copolymers of vinyl lactam, vinyl acetate and vinyl alcohol; polyether-polyester copolymers with crosslinkable side chains; branched polyalkylene glycol-urethane prepolymers; polyalkylene glycol-tetra(meth)acrylate prepolymers; and crosslinkable polyallylamine gluconolactone prepolymers, and mixtures thereof.

12. The process of claim 11, wherein the first and second leachable lubricants, independently of each other, are non-crosslinkable and non-charged hydrophilic polymers selected from the group consisting of polyvinyl alcohols, polyamides, polyimides, polylactone, homopolymers of a vinyl lactam, copolymers of at least one vinyl lactam and at least one hydrophilic vinylic monomer, alkylated polyvinylpyrrolidones, homopolymers of acrylamide, homopolymers of methacrylamide, copolymers of acrylamide and at least one hydrophilic vinylic monomer, copolymers of methacrylamide with at least one hydrophilic vinylic monomer, polyethylene oxide, a polyoxyethylene derivative, poly-N—N-dimethylacrylamide, poly 2 ethyl oxazoline, heparin polysaccharides, polysaccharides, and mixtures thereof.

13. The process of claim 3, wherein the viscosity-enhancing polymer is hydroxymethylcellulose, hydroxyethyl cellulose, hydroxypropylcellulose, or mixture thereof.

14. The process of claim 13, wherein the polyethylene glycol has a molecular weight of 600 daltons.

15. The process of claim 14, wherein the hydrogel lens-forming formulation comprises at least one actinically-crosslinkable prepolymer which are soluble in water, a water-organic solvent mixture or an organic solvent, or meltable at a temperature below about 85° C., wherein the actinically-crosslinkable prepolymer is selected from the group consisting of a water-soluble crosslinkable poly(vinyl alcohol) prepolymer; a water-soluble vinyl group-terminated polyurethane prepolymer; derivatives of a polyvinyl alcohol, derivatives of a polyethyleneimine, derivatives of a polyvinylamine; a water-soluble crosslinkable polyurea prepolymer; crosslinkable polyacrylamide; crosslinkable statistical copolymers of vinyl lactam, MMA and a comonomer; crosslinkable copolymers of vinyl lactam, vinyl acetate and vinyl alcohol; polyether-polyester copolymers with crosslinkable side chains; branched polyalkylene glycol-urethane prepolymers; polyalkylene glycol-tetra(meth)acrylate prepolymers; and crosslinkable polyallylamine gluconolactone prepolymers, and mixtures thereof.

16. The process of claim 15, wherein the first and second leachable lubricants, independently of each other, are non-crosslinkable and non-charged hydrophilic polymers selected from the group consisting of polyvinyl alcohols, polyamides, polyimides, polylactone, homopolymers of a vinyl lactam, copolymers of at least one vinyl lactam and at least one hydrophilic vinylic monomer, alkylated polyvinylpyrrolidones, homopolymers of acrylamide, homopolymers of methacrylamide, copolymers of acrylamide and at least one hydrophilic vinylic monomer, copolymers of methacrylamide with at least one hydrophilic vinylic monomer, polyethylene oxide, a polyoxyethylene derivative, poly-N—N-dimethylacrylamide, poly 2 ethyl oxazoline, heparin polysaccharides, polysaccharides, and mixtures thereof.

17. The process of claim 2, wherein the viscosity-enhancing polymer is hydroxypropylmethyl cellulose.

18. The process of claim 17, wherein the polyethylene glycol has a molecular weight of 600 daltons.

19. The process of claim 18, wherein the hydrogel lens-forming formulation comprises at least one actinically-crosslinkable prepolymer which are soluble in water, a water-organic solvent mixture or an organic solvent, or meltable at a temperature below about 85° C., wherein the actinically-crosslinkable prepolymer is selected from the group consisting of a water-soluble crosslinkable poly(vinyl alcohol) prepolymer; a water-soluble vinyl group-terminated polyurethane prepolymer; derivatives of a polyvinyl alcohol, derivatives of a polyethyleneimine, derivatives of a polyvinylamine; a water-soluble crosslinkable polyurea prepolymer; crosslinkable polyacrylamide; crosslinkable statistical copolymers of vinyl lactam, MMA and a comonomer; crosslinkable copolymers of vinyl lactam, vinyl acetate and vinyl alcohol; polyether-polyester copolymers with crosslinkable side chains; branched polyalkylene glycol-urethane prepolymers; polyalkylene glycol-tetra(meth)acrylate prepolymers; and crosslinkable polyallylamine gluconolactone prepolymers, and mixtures thereof.

20. The process of claim 19, wherein the first and second leachable lubricants, independently of each other, are non-crosslinkable and non-charged hydrophilic polymers selected from the group consisting of polyvinyl alcohols, polyamides, polyimides, polylactone, homopolymers of a vinyl lactam, copolymers of at least one vinyl lactam and at least one hydrophilic vinylic monomer, alkylated polyvinylpyrrolidones, homopolymers of acrylamide, homopolymers of methacrylamide, copolymers of acrylamide and at least one hydrophilic vinylic monomer, copolymers of methacrylamide with at least one hydrophilic vinylic monomer, polyethylene oxide, a polyoxyethylene derivative, poly-N—N-dimethylacrylamide, poly 2 ethyl oxazoline, heparin polysaccharides, polysaccharides, and mixtures thereof.

* * * * *